United States Patent [19]  [11] Patent Number: 4,568,750
Stern  [45] Date of Patent: Feb. 4, 1986

[54] PRECURSORS OF 8-ALKOXY-6,7-DIHYDRO-5-METHYL-9-FLUORO-1-OXO-1H,5H-BENZO[IJ]-QUINOLIZINE-2-CARBOXYLIC ACIDS

[75] Inventor: Richard M. Stern, Cottage Grove, Minn.

[73] Assignee: Riker Laboratories, Inc., St. Paul, Minn.

[21] Appl. No.: 624,406

[22] Filed: Jun. 25, 1984

Related U.S. Application Data

[62] Division of Ser. No. 476,423, Mar. 17, 1983, Pat. No. 4,472,407.

[51] Int. Cl.$^4$ .................. C07D 215/20; C07D 215/00
[52] U.S. Cl. .................................................. 546/165
[58] Field of Search ............... 546/165, 170, 180, 168

[56] References Cited

U.S. PATENT DOCUMENTS

3,896,131  7/1975  Gerster .............................. 546/165

FOREIGN PATENT DOCUMENTS

56-128762  10/1981  Japan ................................. 546/180

OTHER PUBLICATIONS

Gyul'budagyan et al., CA 68: 87119w, *Arm. Khim. Zh.* 20(7), 522–525 (1967) Russ. (abstract).
Franchi et al., CA 68: 114400q, *Farmaco, Ed. Sci.* 22(11), 923–929 (1967) (Ital.) (abstract).
Murugesan et al., CA 91: 91532t, *Synthesis* 1979, (5), 352–354 (Eng.) (abstract).

*Primary Examiner*—Richard A. Schwartz
*Attorney, Agent, or Firm*—Donald M. Sell; James A. Smith; Robert W. Sprague

[57] ABSTRACT

The compounds 5-bromo-6-fluoroquinaldine, 5-bromo-6-fluoro-1,2,3,4-tetrahydroquinaldine, 1-acetyl-5-bromo-6-fluoro-1,2,3,4-tetrahydroquinaldine and diethyl 2-[N-(6-fluoro-5-methoxy-1,2,3,4-tetrahydroquinaldinyl)]-methylenemalonate are intermediates for preparing antimicrobial 8-alkoxy-6,7-dihydro-5-methyl-9-fluoro-1-oxo-1H,5H-benzo[ij]-quinolizine-2-carboxylic acids.

2 Claims, No Drawings

PRECURSORS OF 8-ALKOXY-6,7-DIHYDRO-5-METHYL-9-FLUORO-1-OXO-1H,5H-BENZO[IJ]QUINOLIZINE-2-CARBOXYLIC ACIDS

This is a division of application Ser. No. 476,423, filed Mar. 17, 1983, now U.S. Pat. No. 4,472,407.

TECHNICAL FIELD

This invention relates to derivatives of the heterocyclic system known as benzo[ij]quinolizine. More particularly, it relates to 8-substituted 6,7-dihydro-9-fluoro-5-methyl-1-oxo-1H,5H-benzo[ij]quinolizine-2-carboxylic acids and derivatives thereof. Pharmacological methods of using these compounds as antimicrobial agents, pharmaceutical compositions comprising these compounds, and synthetic intermediates useful for preparing these compounds are also within the scope of the invention.

BACKGROUND OF THE INVENTION

U.S. Pat. No. 3,896,131 broadly describes 6,7-dihydro-5-methyl-1-oxo-1H,5H-benzo[ij]quinolizine-2-carboxylic acids as antimicrobial agents. The patent specifically discloses several compounds substituted by halogen and/or methoxy on the benzo ring. The compound 6,7-dihydro-9-fluoro-5-methyl-1-oxo-1H,5H-benzo[ij]quinolizine-2-carboxylic acid (now known as flumequine) which is disclosed in the aforementioned patent has received the most attention for its antimicrobial activity. It has now been found that the corresponding novel 8-methoxy-9-fluoro compound and 8-ethoxy-9-fluoro compound are much more potent and have a broader spectrum of antimicrobial activity than the compounds of the prior art.

DESCRIPTION OF THE INVENTION

The present invention relates to 8-substituted 6,7-dihydro-9-fluoro-5-methyl-oxo-1H,5H-benzo[ij]quinolizine-2-carboxylic acids and derivatives thereof. This invention also relates to the pharmacological use of the compounds as antimicrobial agents and to pharmaceutical compositions comprising these compounds. The invention also relates to synthetic intermediates useful for preparing these compounds.

Specifically, this invention relates to the novel compounds of Formula I

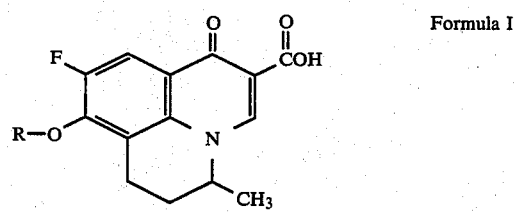

Formula I wherein R is a lower alkyl group; and derivatives thereof selected from the acyl chloride, esters, alkylaminoalkyl ester salts and pharmaceutically acceptable carboxylate salts. Thee compounds of Formula I and certain of their derivatives are useful antimicrobials.

Compounds of the invention have an optically active carbon at the 5 position. All such optical isomers are included within the scope of the invention.

The phrase "lower alkyl" as used herein designates a straight or branched-chain alkyl group containing 1 to about 4 carbon atoms. The preferred lower alkyl groups are methyl and ethyl, and the most preferred lower alkyl group is methyl.

It is well known to the art that pharmaceutically acceptable salts such as alkali metal, alkaline earth, aluminum, iron, silver and other metal and amine salts of pharmaceutically active acids are the equivalents of the acids in terms of activity, and in some cases may even offer advantages in absorption, formulation and the like. Pharmaceutically-acceptable carboxylate salts of the free acid compounds of the invention are readily prepared by reaction of the acid with a base and subsequent evaporation to dryness. The base may be organic, for example, sodium methoxide or an amine, or inorganic, for example, sodium hydroxide. Alternatively, the cation of a carboxylate salt, for example, sodium, may be displaced by a second cation such as calcium or magnesium when the salt of the second cation is more insoluble in a selected solvent.

Other useful derivatives of the compounds of the invention include the acyl chlorides, esters and alkylaminoalkyl ester salts thereof. In the acyl chloride derivatives, the hydroxyl portion of the carboxylic acid group is removed and replaced with chlorine. In the ester derivatives, the hydrogen portion of the carboxylic acid group is replaced with an alkyl or substituted alkyl, preferably an alkylaminoalkyl group.

Esters and the acyl chlorides of the compounds of the invention may be obtained as intermediates during the preparation of the acidic compounds. In some cases, the esters may be prepared directly using standard synthetic methods. These esters and acyl chlorides exhibit antimicrobial activity, but they are primarily of interest as synthetic intermediates, although in some instances hydrolyzable or salt-forming esters may be of interest as therapeutic agents. Preferred esters are alkyl esters and alkylaminoalkyl esters having one to four carbon atoms in the alkyl group(s). Especially preferred are alkylaminoalkyl esters such as the dimethylaminoethyl esters which will form salts, for example, hydrochlorides.

Ester derivatives are readily prepared by reacting a free acid of Formula I with thionyl chloride to provide the novel acyl chloride derivative. The acyl chloride is reacted with the appropriate alcohol to provide the desired ester.

The antimicrobial activity of the compounds of the present invention can be demonstrated by the known, standard plate dilution method for bacterial susceptibility testing of fastidious microorganisms toward antibiotics, sulfonamides and other chemotherapeutic agents. Tryptone soy agar (oxoid) of the following composition is the culture medium.

| | |
|---|---|
| Oxoid tryptone | 15 g. |
| Oxoid soy peptone | 2 g. |
| Sodium chloride | 5 g. |
| Oxoid agar-agar No. 3 | 15 g. |
| Water | 1 liter |

Using this test, certain of the compounds of the invention have been found to have a broad spectrum of activity against gram-positive and gram-negative microorganisms.

The compounds of the invention are active against microorganisms either in the absence or presence of 10 percent horse serum.

The test procedure used to determine activity as employed in connection with the present invention provides information on the amount of a compound which gives complete inhibition, partial inhibition or no inhibition of microbial growth on the agar plates. In the tests, the selected compound is added to the agar medium to give concentrations of zero, one, ten and one hundred milligrams per liter. A series of plates with these concentrations is prepared. Ten percent horse serum is added to one series of such plates. Aliquots of broth culture of any of twelve species of microorganisms are innoculated onto the agar plates containing the various compound concentrations. The plates are incubated at 37° C. in a 10 percent carbon dioxide atmosphere for 18–24 hours. The microbial growth on each plate is read visually, and minimum inhibitory concentrations (for partial or complete inhibition) are recorded. Some of the microoorganisms which may be used for this test are:

1. *Staphylococcus aureus*
2. *Bacillus subtilis*
3. *Escherichia coli*
4. *Pseudomonas aeruginosa*
5. *Streptococcus sp.**
6. *Aspergillus niger*
7. *Candida albicans*
8. *Acinetobacter lwoffi*
9. *Acinetobacter anitratum*
10. *Klebsiella pneumoniae*
11. *Streptococcus fecaelis*
12. *Serratia marcescens*

*Strains isolated from dental caries in rats or hamsters at the National Institute of Dental Health and grown in PFY or APT agar.

The compounds of the invention possess antimicrobial activity towards one or more of the above microorganisms. Of specific significance is the high level of activity of 6,7-dihydro-9-fluoro-8-methoxy-5-methyl-1-oxo-1H,5H-benzo[ij]quinolizine-2-carboxylic acid and 6,7-dihydro-8-ethoxy-9-fluoro-5-methyl-1-oxo-1H,5H-benzo[ij]quinolizine-2-carboxylic acid and their carboxylate and alkylaminoalkyl ester salts against *Pseudomonas aeruginosa*, a particularly bothersome species associated with many topical infections. This type of activity is relatively unusual in benzoquinolizine-type antibacterials.

It will be understood by those skilled in the art that the species used are representative indicator species, as it would be impractical to screen against all bacteria. It is well known in the art that broad spectrum activity can be predicted on the basis of activity shown against selected representative bacterial species.

The compounds of the invention are active when administered orally to animals. They are excreted in the urine, and are effective urinary tract antibacterials in mammals. They may also be used in the treatment of pulmonary infections, soft tissue infections, burn infections and bacteremias.

Compounds of the invention are active against microorganisms in vitro or topically. In vitro activity is useful in itself, since antimicrobial agents may be used for disinfecting and sterilizing, e.g., medical and dental equipment, as components of disinfecting solutions.

The acute oral toxicity of the compounds of the invention generally is moderate to low compared with the effective oral dose, and they have an acceptable therapeutic ratio ($LD_{50}/ED_{50}$) of greater than 80.

The acidic compounds of the invention are generally white crystalline materials when purified. They are substantially insoluble in water, lower alcohols or hydrocarbons and are more soluble in halogenated solvents, N,N-dimethylformamide and the like. The salts, especially the alkali metal salts, have appreciable solubility in water and lower alcohols.

The compounds of the invention may be formulated by incorporating them into conventional pharmaceutical carrier materials, either organic or inorganic, which are suitable for oral or intraperitoneal application. For in vitro or topical use, simple aqueous solutions or suspensions are most conveniently employed. For this purpose, concentrations of the order of 100 parts per million up to about 5 parts per thousand are suitable, and the formulation is used by immersing objects to be treated therein, or by local application to an infected area.

The amount of a compound used to treat, for example, a microbial urinary infection by oral administration will be an effective amount less than a toxic amount. The amount to be administered to control an infection will depend on the species, sex, weight, physical condition and many other factors, but this judgment is well within the skill of the medical art. Usually the amount will be less than 100 mg/kg per dose. Conveniently this is administered in the form of the usual pharmaceutical preparations such as capsules, tablets, emulsions, solutions and the like. Excipients, fillers, coatings, etc., are employed with tablets or capsules, as is well known in the art.

It is known to the art that antimicrobial agents are used as growth promoters in various animal and bird species. Although not yet verified, it is inferred from their outstanding antimicrobial activity that the compounds of the invention can be used for this purpose also. The compounds of the invention may also be used for the control of microbial (e.g., *Erwinia amylovora*) infections of plants, e.g., by spraying or dusting a formulation of these compounds on the affected area.

The acid compounds of the invention may be prepared as described in the following reaction scheme wherein R is as defined previously; M is sodium, lithium or potassium; and alk and each $R^1$ are independently lower alkyl, and preferably methyl or ethyl.

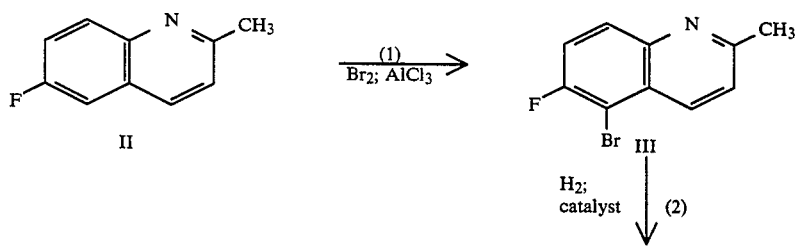

In step (1) of the reaction scheme, the known compound 6-fluoroquinaldine of Formula II is brominated with liquid bromine in the presence of aluminum chloride in a suitable solvent such as 1,2-dichoroethane. The reaction mixture is heated at reflux for several hours to provide the novel intermediate 5-bromo-6-fluoroquinaldine of Formula III.

In step (2), 5-bromo-6-fluoroquinaldine of Formula III is reduced to provide the novel intermediate 5-bromo-6-fluoro-1,2,3,4-tetrahydroquinaldine of Formula IV. The reduction is conducted in a Paar apparatus using, for example, platinum on charcoal as a catalyst. The reduction is conducted in a solvent such as acetic acid.

The 5-bromo-6-fluoro-1,2,3,4-tetrahydroquinaldine intermediate of Formula IV is reacted in step (3) with acetic anhydride to provide the novel intermediate 1-acetyl-5-bromo-6-fluoro-1,2,3,4-tetrahydroquinaldine of Formula V. The reaction is conducted by heating the reaction mixture, for example, using a steam bath.

In step (4), 1-acetyl-5-bromo-6-fluoro-1,2,3,4-tetrahydroquinaldine of Formula V is reacted with a metal alkoxide of Formula VA such as a sodium alkoxide to provide a 5-alkoxy-6-fluoro-1,2,3,4-tetrahydroquinaldine of Formula VI. The reaction is conducted in the presence of cuprous iodide and collidine.

The 5-alkoxy-6-fluoro-1,2,3,4-tetrahydroquinaldine of Formula VI is condensed with an alkyl alkoxymethylenemalonate of Formula VIA in step (5). The preferred dialkyl alkoxymethylenemalonate is diethyl ethoxymethylenemalonate since it is most readily available. The condensation reaction may be conducted in the absence of solvent, in which case the reactants are heated at a temperature of 100° to 200° C. for several hours until the reaction is complete as determined by chromatographic analysis. It is preferred that the reaction be heated at a temperature of 140°–150° C. for two hours. Alternatively, the reaction may be conducted in the presence of an inert organic solvent such as toluene or xylene which forms an azeotropic mixture with the alcohol formed upon condensation of the dialkyl alkoxymethylenemalonate (e.g., ethanol where diethyl ethoxymethylenemalonate is employed in step (4)). When such a solvent is employed, the reaction mixture is heated at its reflux temperature and the azeotropic mixture comprising the alcohol and the organic solvent is collected, for example, in a Dean Stark trap. Fresh organic solvent is generally added to the reaction mixture as the solvent is depleted during distillation. Removal of the alcohol from the reaction mixture drives the condensation reaction to substantial completion and increases the yield. The product of step (5) is the novel dialkyl 2-[N-(6-fluoro-5-methoxy-1,2,3,4-tetrahydroquinaldinyl)]methylenemalonate of Formula VII. This intermediate may be isolated, e.g., as an oil or a solid, or the product of step (5) may be used directly in step (6) below without isolation of the intermediate.

In step (6) the intermediate of Formula VII is cyclized to form the ester of Formula VIII. The cyclization step is carried out by heating the intermediate of Formula VII in the presence of polyphosphoric acid. The temperature of the reaction is preferably about 100° C. Alternatively, cyclization of the intermediate of Formula VII is carried out in the presence of phosphorus oxychloride by refluxing the reaction mixture for several hours, evaporating the excess phosphorus oxychloride and refluxing the residue in the presence of water.

The ester of Formula VIII is saponified in step (7) by conventional means to provide a carboxylic acid of Formula I.

Compounds of the invention may also be prepared by ether cleavage of an 8-alkoxy compound of Formula I using, for example, 48% hydrobromic acid, followed by alkylation of the resulting novel 8-hydroxy compound.

The following examples are provided to illustrate the synthetic methods useful to obtain compounds of the invention, and are not intended to be limiting of the invention.

EXAMPLE 1

Synthesis of 6,7-dihydro-9-fluoro-8-methoxy-5-methyl-1-oxo-1H,5H-benzo[ij]quinolizine-2-carboxylic Acid Part A. Preparation of 5-bromo-6-fluoroquinaldine A solution of 100.7 g (0.625 mole) of 6-fluoroquinaldine in 125 ml of 1,2-dichloroethane was added slowly over 30 minutes to 126.5 g (0.95 mole) of aluminum chloride in 125 ml of 1,2-dichloroethane. The mixture was heated to 70° to 80° C., and 32 ml of liquid bromine was added dropwise over 4 hours. The mixture was stirred and heated at 80° to 85° C. for 20 hours, and was then poured over 1.5 liters of ice. After stirring thoroughly, the mixture was acidified with 50 ml of concentrated hydrochloric acid. Zinc chloride (85 g) was added, and the mixture was stirred for 10 minutes. The mixture was cooled in an ice bath, and the solid product was separated by filtration and washed sequentially with cold 3N hydrochloric acid and dichloromethane. The solid was slurried in water and neutralized with concentrated ammonium hydroxide. Filtration provided a solid which was dissolved in toluene. The solution was dried over magnesium sulfate, and then evaporated to provide a residue which was recrystallized from hexane to provide 5-bromo-6-fluoroquinaldine. The structure was confirmed by a nuclear magnetic resonance spectral analysis.

Part B. Preparation of 5-bromo-6-fluoro-1,2,3,4-tetrahydroquinaldine

To a solution of 20 g of 5-bromo-6-fluoroquinaldine in 150 ml of glacial acetic acid was added 2.0 g of platinum on charcoal. The mixture was hydrogenated on a Paar apparatus at a temperature of about 20° C. until the theoretical amount of hydrogen was taken up. The mixture was then filtered through celite to provide a solution of 5-bromo-6-fluoro-1,2,3,4-tetrahydroquinaldine. Evaporation of the solvent provides the desired intermediate. This intermediate could be used directly in Part C below without purification.

Part C. Preparation of N-acetyl-5-bromo-6-fluoro-1,2,3,4-tetrahydroquinaldine

To 6.0 g of 5-bromo-6-fluoro-1,2,3,4-tetrahydroquinaldine was added 50 ml of acetic anhydride and one drop of concentrated sulfuric acid. The solution was heated on a steam bath for two hours, then cooled to about 20° C. The solution was basified with 10% sodium hydroxide solution. The solution was extracted with chloroform, and the chloroform extracts were evaporated to provide an oil which was distilled in vacuo to provide N-acetyl-5-bromo-6-fluoro-1,2,3,4-tetrahydroquinaldine. The structural assignment was supported by nuclear magnetic resonance spectral analysis.

Part D. Preparation of 6-fluoro-5-methoxy-1,2,3,4-tetrahydroquinaldine

Sodium methoxide was prepared from 1.2 g of sodium in 12 ml of methanol. To this solution was added 4.0 g of N-acetyl-5-bromo-6-fluoro-1,2,3,4-tetrahydroquinaldine, 1.6 g of cuprous iodide and 50 ml of dry collidine. The mixture was heated at its reflux temperature for about 16 hours, then evaporated. The residue was extracted with chloroform, the extracts were dried over magnesium sulfate, and the solvent was evaporated to provide a residue. The residue was triturated with hexane and separated by filtration, and the filtrate was evaporated to provide 1.2 g of 6-fluoro-5-methoxy-1,2,3,4-tetrahydroquinaldine. The structural assignment was supported by nuclear magnetic resonance spectral analysis.

Part E. Prepartion of 6,7-dihydro-9-fluoro-8-methoxy-5-methyl-1-oxo-1H,5H-benzo[ij]quinolizine-2-carboxylic Acid A mixture of 1.2 g of 6-fluoro-5-methoxy-1,2,3,4-tetrahydroquinaldine and 2.5 g of diethyl ethoxymethylenemalonate was heated at 140° C. for 3 hours, and was then cooled to 100° C. To the crude hot diethyl 2-[N-(6-fluoro-5-methoxy-1,2,3,4-tetrahydroquinaldinyl)]methylenemalonate was added 25 g of polyphosphoric acid, and the mixture was heated on a steam bath for one hour. The mixture containing ethyl 6,7-dihydro-9-fluoro-8-methoxy-5-methyl-1-oxo-1H,5H-benzo[ij]quinolizine-2-carboxylate was cooled to about 20° C., diluted with an equal volume of water and basified with 50% sodium hydroxide solution. This solution was heated at its reflux temperature for two hours and filtered hot through celite. The filtrate was cooled to about 20° C. and acidified with concentrated hydrochloric acid. The solid was separated by filtration to provide 1.2 g of off-white 6,7-dihydro-9-fluoro-8-methoxy-5-methyl-1-oxo-1H,5H-benzo[ij]quinolizine-2-carboxylic acid. Recrystallization from aqueous N,N-dimethylformamide provided pure product, m.p. 234°–236° C. Analysis: Calculated for $C_{15}H_{14}FNO_4$: %C,61.8; %H,4.8; %N,4.8; Found: %C,61.7; %H,4.6; %N,4.8.

EXAMPLE 2

A solution of 1.2 g of 6,7-dihydro-9-fluoro-8-methoxy-5-methyl-1-oxo-1H,5H-benzo[ij]quinolizine-2-carboxylic acid in 25 ml of 48% hydrobromic acid was heated at reflux for three hours, and was then cooled and diluted with about 100 ml of water. The product was separated by filtration and recrystallized from aqueous N,N-dimethylformamide to provide white solid 6,7-dihydro-9-fluoro-8-hydroxy-5-methyl-1-oxo-1H,5H-benzo[ij]quinolizine-2-carboxylic acid hydrate, m.p. 293°–294° C. Analysis: Calculated for $C_{14}H_{12}FNO_4 \cdot 0.25H_2O =$ %C,59.7;%H,4.5;%N,5.0; Found: %C,59.5;%H,4.2;%N,5.0.

EXAMPLE 3

A solution of 1.0 g of 6,7-dihydro-9-fluoro-8-hydroxy-5-methyl-1-oxo-1H,5H-benzo[ij]quinolizine-2-carboxylic acid, 1.4 g of potassium carbonate and 2.0 ml of diethyl sulfate in 15 ml of dimethyl sulfoxide was heated at its reflux temperature for sixteen hours. The solution was then evaporated to dryness by heating on a steam bath under a stream of nitrogen. Fifty ml of 1% aqueous sodium hydroxide solution was added to the resulting residue. The mixture was heated on a steam bath for one hour, acidified with concentrated hydrochloric acid and cooled. The solid was separated by filtration and recrystallized from aqueous ethanol to provide 6,7-dihydro-8-ethoxy-9-fluoro-5-methyl-1-oxo-1H,5H-benzo[ij]quinolizine-2-carboxylic acid, m.p. 208°–210° C. (dec.). Analysis: Calculated for $C_{16}H_{16}FNO_4$: %C,63.0;%H,5.3;%N, 4.6; Found: %C,62.9;%H,5.3;%N,4.6.

method described hereinabove. The tests were run in the absence (Column A) and in the presence (Column B) of horse serum as described hereinabove and amounts of the antimicrobial agent were as indicated. The results (recorded at the minimum concentrations in milligrams of the active antimicrobial agent per liter which provide partial or complete inhibition of the growth of the indicated microorganisms) are shown in the table below:

| COMPOUND | STREPTOCOCCUS SPECIES | | STAPHYLOCOCCUS AUREUS | | ESCHERICIA COLI | | PSEUDOMONAS AERUGINOSA | |
| --- | --- | --- | --- | --- | --- | --- | --- | --- |
| | A | B | A | B | A | B | A | B |
| 6,7-dihydro-9-fluoro-8-methoxy-5-methyl-1-oxo-1H,5H—benzo[ij]quinolizine-2-carboxylic acid | 10 | 10* | 1 | 1 | 0.1 | 0.1 | 10 | 10* |
| 6,7-dihydro-8-ethoxy-9-fluoro-5-methyl-1-oxo-1H,5H—benzo[ij]quinolizine-2-carboxylic acid | 10 | 10 | 0.1* | 0.1* | 0.1 | 0.1 | 10 | 10* |
| 6,7-dihydro-9-fluoro-5-methyl-1-oxo-1H,5H—benzo[ij]quinolizine-2-carboxylic acid (Flumequine) | 100 | 100 | 10 | 10 | 1 | 1 | 100 | 100 |
| 6,7-dihydro-9-methoxy-5-methyl-1-oxo-1H,5H—benzo[ij]quinolizine-2-carboxylic acid | 100 | 100 | 100 | 100 | 10 | 10 | >100 | >100 |
| 6,7-dihydro-8-methoxy-5-methyl-1-oxo-1H,5H—benzo[ij]quinolizine-2-carboxylic acid | 100 | 100 | 10 | 10 | 1 | 1 | 100 | 100 |
| 8-chloro-6,7-dihydro-9-methoxy-5-methyl-1-oxo-1H,5H—benzo[ij]quinolizine-2-carboxylic acid | 100 | 100 | 10 | 10 | 10 | 10 | >100 | >100 |
| 6,7-dihydro-8,9-dimethoxy-5-methyl-1-oxo-1H,5H—benzo[ij]quinolizine-2-carboxylic acid | >100 | >100 | >100 | >100 | 100* | 100* | >100 | >100 |

*partial inhibition

EXAMPLE 4

The antibacterial activity of 6,7-dihydro-9-fluoro-8-methoxy-5-methyl-1-oxo-1H,5H-benzo[ij]quinolizine-2-carboxylic acid and 6,7-dihydro-8-ethoxy-9-fluoro-5-methyl-1-oxo-1H,5H-benzo[ij]quinolizine-2-carboxylic acid of the present invention and that of several 6,7-dihydro-5-methyl-1-oxo-1H,5H-benzo[ij]quinolizine-2-carboxylic acids disclosed in U.S. Pat. No. 3,896,131 was determined using the standard plate dilution It is seen that the 8-methoxy and 8-ethoxy compounds of the present invention exhibit significantly greater activity than the compounds of the prior art.

What is claimed is:

1. The compound 1-acetyl-5-bromo-6-fluoro-1,2,3,4-teetrahydroquinaldine.

2. The compound diethyl 2-[N-(6-fluoro-5-methoxy-1,2,3,4-tetrahydroquinaldinyl)]methylenemalonate.

* * * * *